United States Patent [19]
Taheri

[11] Patent Number: 5,919,207
[45] Date of Patent: Jul. 6, 1999

[54] PERCUTANEOUS ARTERIAL CLOSURE WITH STAPLES

[76] Inventor: Syde A. Taheri, 1275 Delaware Ave., Buffalo, N.Y. 14209

[21] Appl. No.: 09/088,918

[22] Filed: Jun. 2, 1998

[51] Int. Cl.[6] ................................................. A61B 17/04
[52] U.S. Cl. ........................ 606/219; 606/139; 606/144; 606/148
[58] Field of Search .................................. 606/139, 144, 606/148, 219

[56] References Cited

U.S. PATENT DOCUMENTS

| | | | |
|---|---|---|---|
| 4,944,443 | 7/1990 | Oddsen et al. | 227/19 |
| 5,433,727 | 7/1995 | Sideris | 606/213 |
| 5,732,872 | 3/1998 | Bolduc et al. | 227/176.1 |
| 5,782,861 | 7/1998 | Cragg et al. | 606/216 |
| 5,792,179 | 8/1998 | Sideris | 606/213 |
| 5,810,884 | 9/1998 | Kim | 606/213 |

*Primary Examiner*—Gary Jackson
*Attorney, Agent, or Firm*—Hodgson, Russ, Andrews, Woods & Goodyear LLP

[57] ABSTRACT

A method and apparatus for percutaneous arterial closure with staples. The apparatus comprises a triple lumen catheter, two j-shaped guide wires, a vascular stapler, and a tubular member. The method and apparatus provide for closure of arterial punctures that are typically created during catheterization. The method and apparatus provide a percutaneous method that reduces the likelihood of bleeding and the formation of false aneurysms. The method comprises inserting the triple lumen catheter in the arterial opening to deploy a pair of guide wires having projections at the end. The catheter is removed and the projections on the end of the guide wires are engaged with the arterial wall around the opening. The guide wires are then twisted to close the opening. Next, a stapler is moved down the guide wires to the site of the opening where staples are inserted to close the opening. Then, the tubular member slides over the guide wires and straightens the projections for removal from inside the artery. The tubular member and the guide wires are then removed from arterial opening and the skin is closed with a normal staple.

19 Claims, 9 Drawing Sheets

PERCUTANEOUS ARTERIAL CLOSURE WITH STAPLES

FIELD OF THE INVENTION

The present invention relates generally to arterial catheterization and more particularly to percutaneous arterial closure after catheterization.

BACKGROUND OF THE INVENTION

There are approximately five million cases yearly of arterial catheterization in the United States. Approximately seven hundred thousand of these cases will have serious complications requiring surgical intervention. Surgical intervention for primary closure of the arterial injury requires an operating team, a standby anesthetist, and an extra day of hospitalization, and as a result can be quite expensive. More conservative treatments such as ultrasound, compression, bed rest and thrombin injections into false aneurysms have been attempted, but these techniques have failed to treat the serious complications of the arterial catheterization.

What is needed is an apparatus and a method for percutaneous arterial closure after catheterization that is nonsurgical and that prevents bleeding and the formation of false aneurysms.

SUMMARY OF THE INVENTION

The present invention solves the above described problem by allowing an interventionist to close an arterial puncture after catheterization in order to prevent complications, such as bleeding and false aneurysm.

The system consists of a triple lumen catheter, two coaxial graded, j-shaped guide wires, and vascular staples for closing the arterial opening. After catheterization of an artery, the angiography catheter is removed, and the guide wires are left inside the artery. The graded angiography catheter is replaced with the triple lumen catheter of the present invention. Two j-shaped coaxial guide wires are preinserted into the catheter and are carried into the arterial lumen. The catheter is then removed from the puncture site, and the j-shaped or hook guide wires are inserted into the walls of the artery on opposite sides of the arterial puncture.

The j-shaped guide wires are then twisted to close the arterial puncture. As a result, the wires become crossed. A vascular stapler is passed over the crossed guide wires through the body's lumen. The vascular stapler is then moved down toward the arterial opening. While moving downward and crossing the hook guide wires, friction between the stapler and the guide wires urges the guide wires to approximate the edges of the arterial opening. The stapler continues along the guide wires all the way to the arterial opening. After confirming the stapler's proximity to the approximated edge of the arterial opening, the staples are released to close the edge of the arterial puncture. The hook guide wire is then straightened and removed by passing a tubular member over it. Finally, the skin opening is approximated with a standard staple.

Accordingly, it is an object of the present invention to provide for percutaneous closure of an arterial opening that prevents bleeding and false aneurysm formation.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

Figure 1:
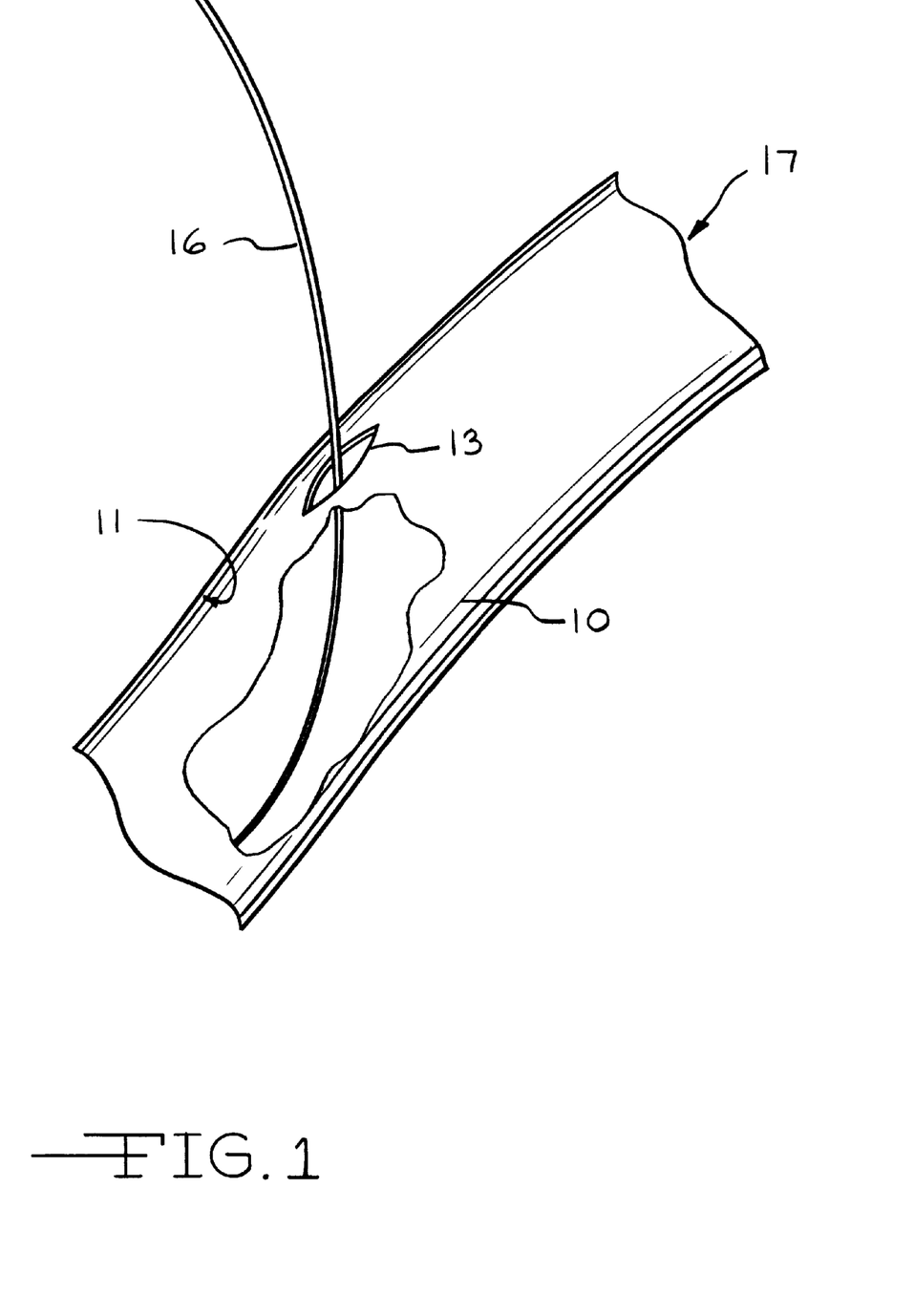
FIG. 1 is a schematic drawing of an arterial catheterization.

In FIG. 1, an artery 10 having inner walls 11 and an arterial puncture 13 has a guide wire 16 extending from the lumen 17 of the artery. The guide wire 16 is inserted into the artery 10 to provide guidance for an angiography catheter (not shown) during catheterization.

Figure 2:
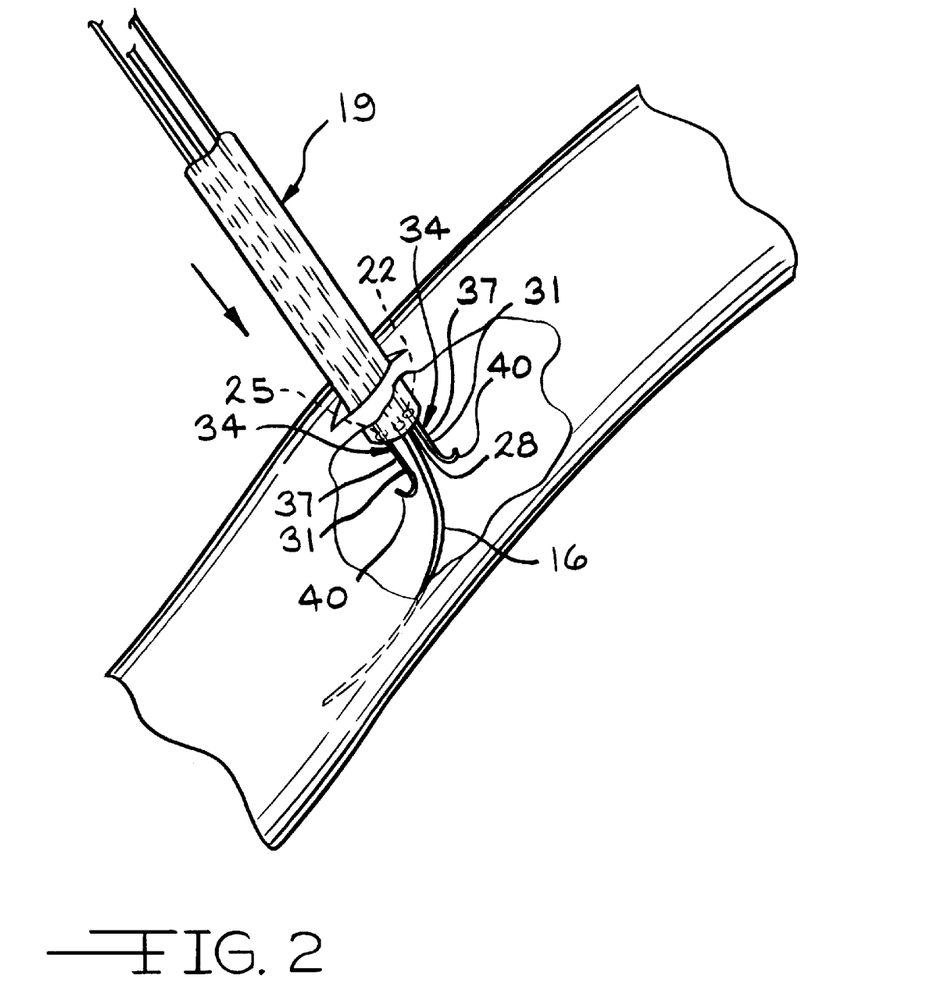
FIG. 2 is a perspective view of the catheter and guide wires of the present invention.

Turning to FIG. 2, a triple lumen catheter 19 has a first lumen 22 and a second lumen 25. The first lumen 22 and the second lumen 25 are preferably cylindrically shaped and disposed on opposite sides of the inside of catheter 19. The third lumen 28 is defined by the remaining space inside the catheter 19 around the first lumen 22 and second lumen 25. The guide wire 16 which remains from the catheterization procedure is threaded through the third lumen 28 to guide the catheter 19 into the artery 10.

Disposed inside the first lumen 22 and the second lumen 25 are a pair of j-shaped guide wires 31. The guide wires 31 are preferably elongate and deformable at an end 34. The end 34 of the guide wires 31 curves away from the body 37 of the guide wire 31 to form a projection 40. The body 37 and the projection 40 typically form a j-shape. However, as described below, the projections 40 can be deformed into alignment with the body 37.

It should be understood that while a triple lumen catheter is preferred, the present invention should not be so limited. An assembly having a pair of spaced apart j-shaped guide wires 31 disposed inside a lumen with the ends 34 of the guide wires 31 extending in spaced apart directions is acceptable for practicing the present invention. Preferably, the ends 34 extend in generally opposite directions.

Figure 3:
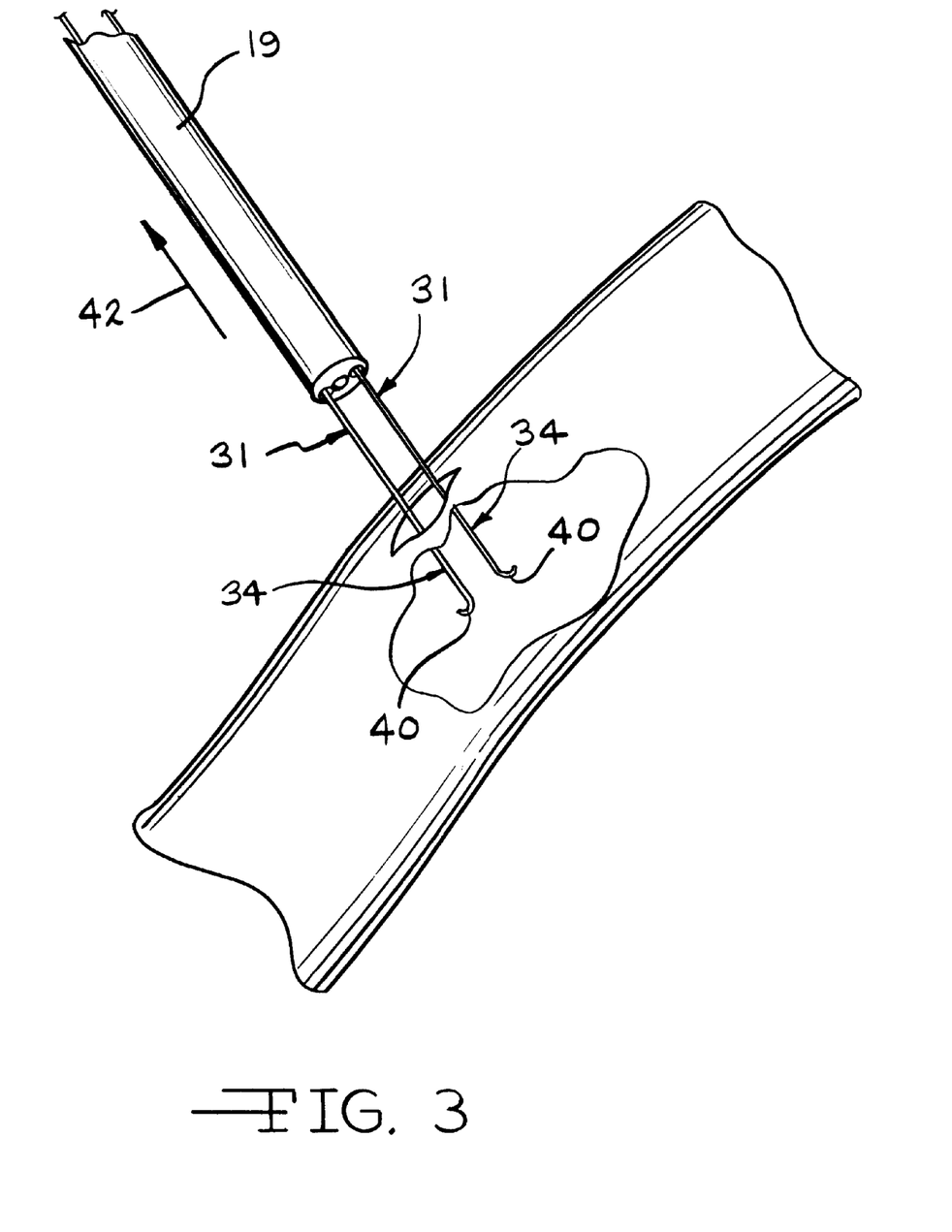
FIG. 3 is a perspective view of the catheter being removed from the artery.

In FIG. 3, arrow 43 indicates the movement of the catheter 19 out of the arterial puncture 13. The guide wires 31 with projections 40 remain inside the artery 10 after the catheter 19 is removed.

Figure 4:
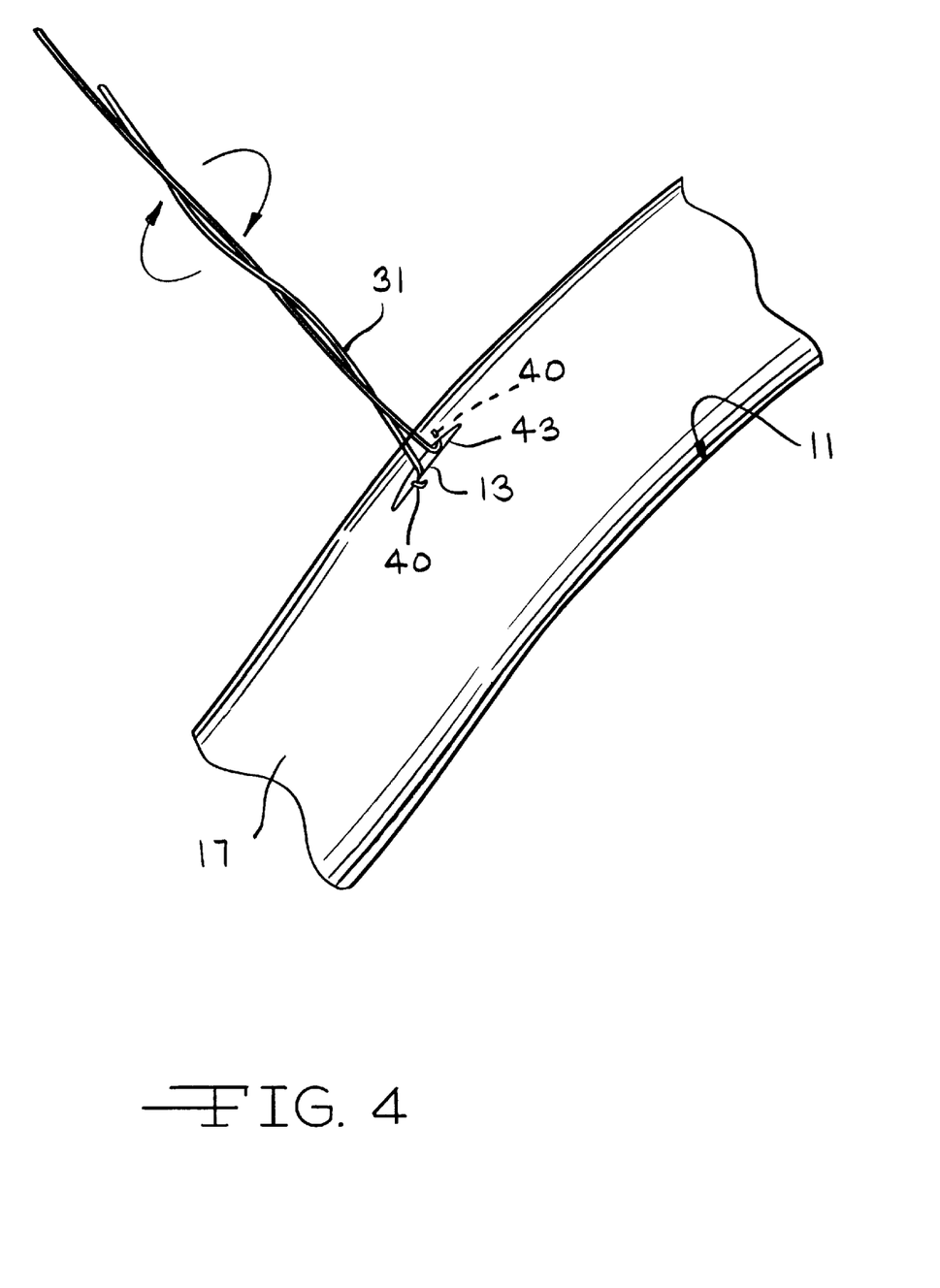
FIG. 4 is a perspective view of the guide wires being twisted to close the arterial opening.

In FIG. 4, the projections 40 engage with the inner walls 11 on opposite sides of the arterial puncture 13. In order to approximate the opening 43 created by the arterial puncture 13, the guide wires 31 are twisted.

Figure 5:
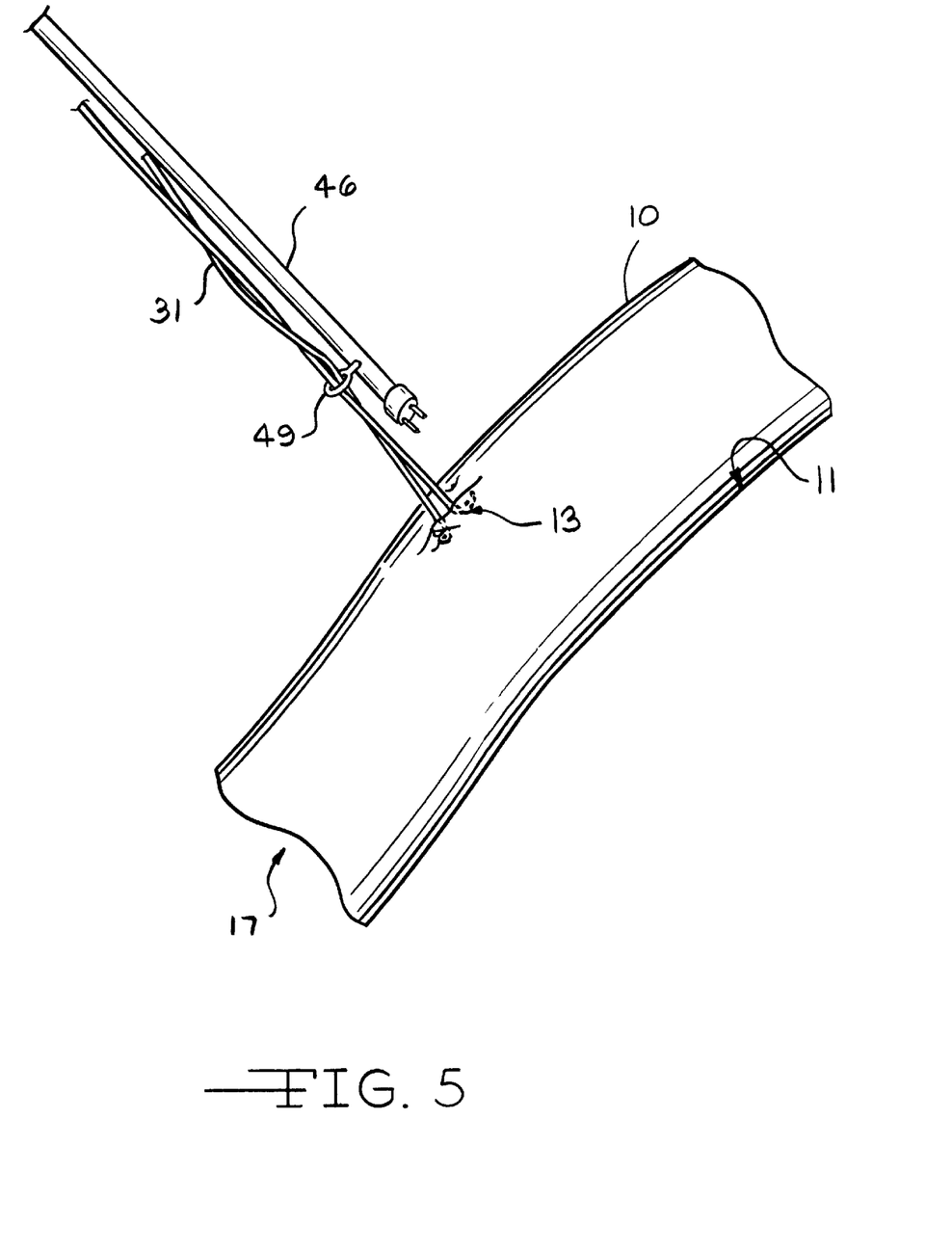
FIG. 5 is a perspective view of the stapler of the present invention being passed over the guide wires.

Turning to FIG. 5, a vascular stapler 46 has an eyelet 49 attached to the body of the stapler 46. The stapler 46 is preferably a standard vascular stapler having an eyelet 49 or other opening for sliding over the guide wires 31. The vascular stapler 46 is guided through the incision in the skin by the eyelet 49 which slides over the guide wires 31. In this manner, the stapler 46 is guided to the immediate area of the artery 10 around the arterial puncture 13.

Figure 6:
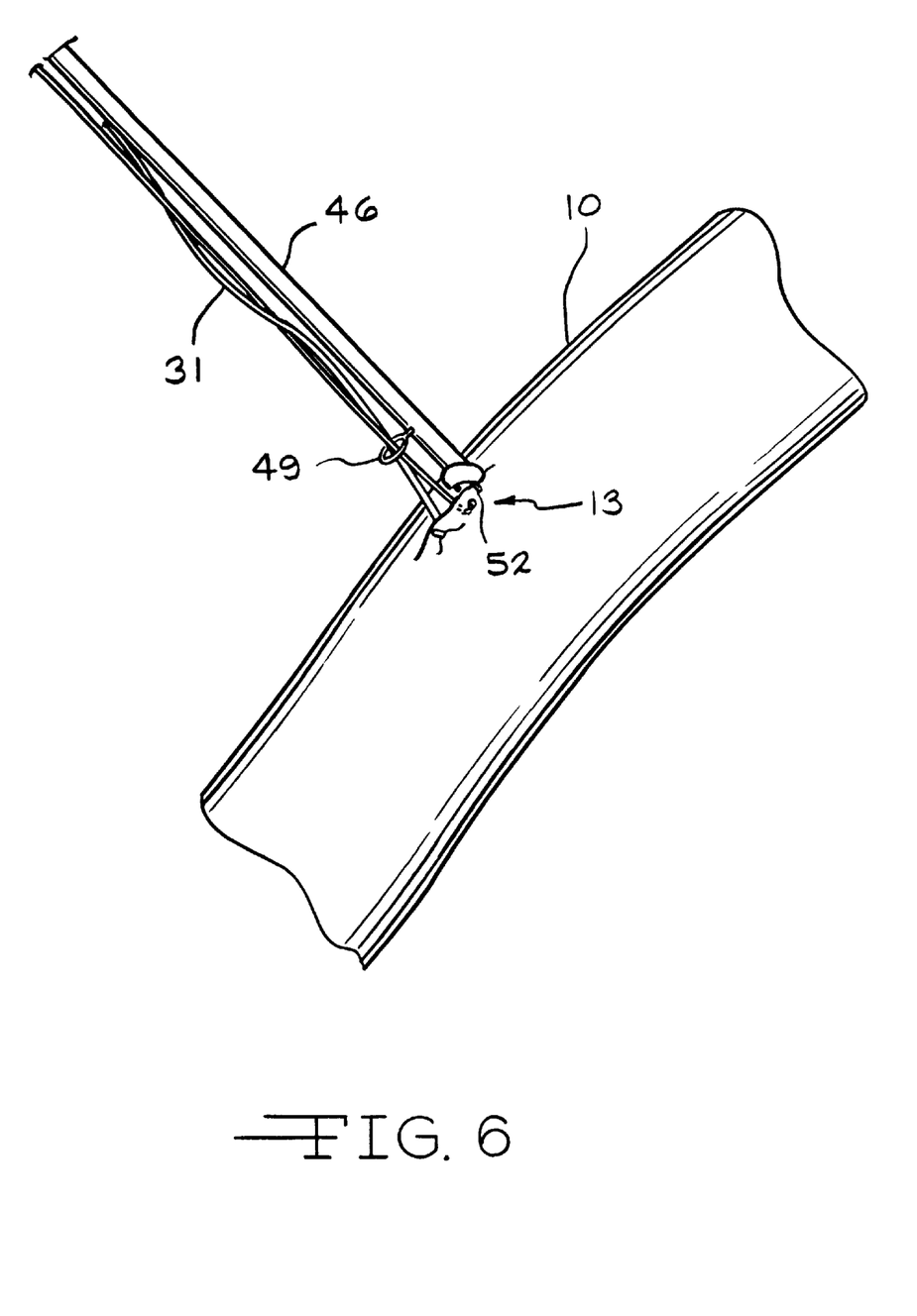
FIG. 6 is a perspective view of the staples being deployed to close the arterial opening.

The eyelet 49 sliding over the guide wires 31 also achieves an additional benefit. The friction of the eyelet 49 on the guide wires 31 creates an additional force that urges the two sides of the opening 43 to close tighter. As shown in FIG. 6, once the stapler 46 has traveled all the way to the artery 10 and the position of the stapler 46 is verified by X-Ray or other detection means, the stapler 46 closes the opening 43 by inserting staples 52 into the surrounding tissue.

Figure 7:
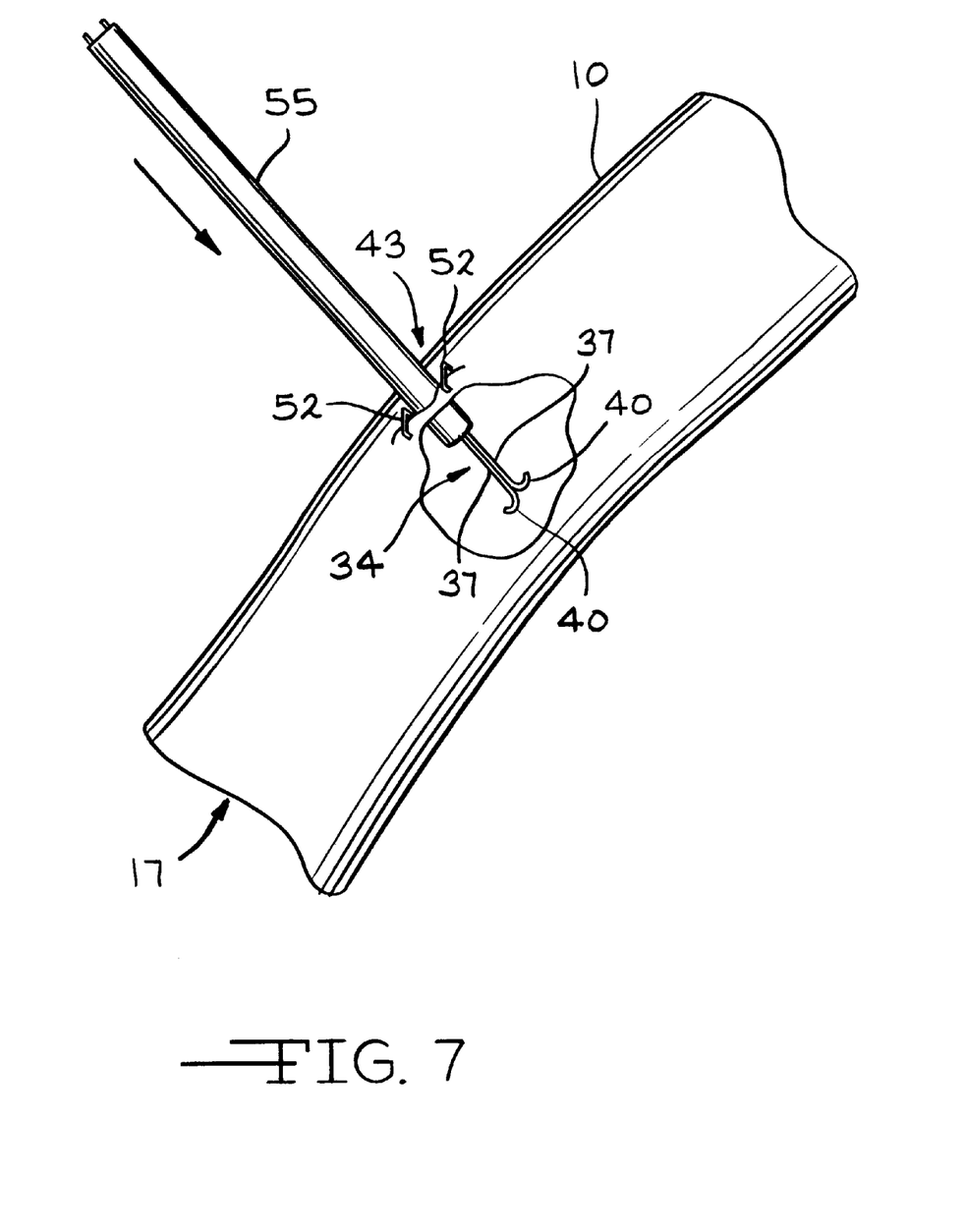
FIG. 7 is a perspective view of the tubular member of the present invention passing over the guide wires.

Turning to FIG. 7, once the staples 52 are inserted to close the opening 43, a tubular member 55, which is preferably elongate and thin, is inserted into the artery 10 over the guide wires 31. The tubular member 55 passes through the opening 43 into the lumen 17 of the artery 10. Once inside the artery 10, the tubular member 55 slides over the end 34 of the guide wires 31 causing the projections 40 to be straightened out so that they can be removed. As described above, the end 34 of the guide wires 31 is deformable such that after the staples 52 have been inserted to close the opening 43, the guide wires 31 can be straightened by passing the tubular member 55 over the outside of the guide wires 31. Passing the tubular member 55 over the guide wires 31 bends the projections 40 back into alignment with the body 37 of the guide wires 31 (best shown in FIG. 9).

Figure 8:
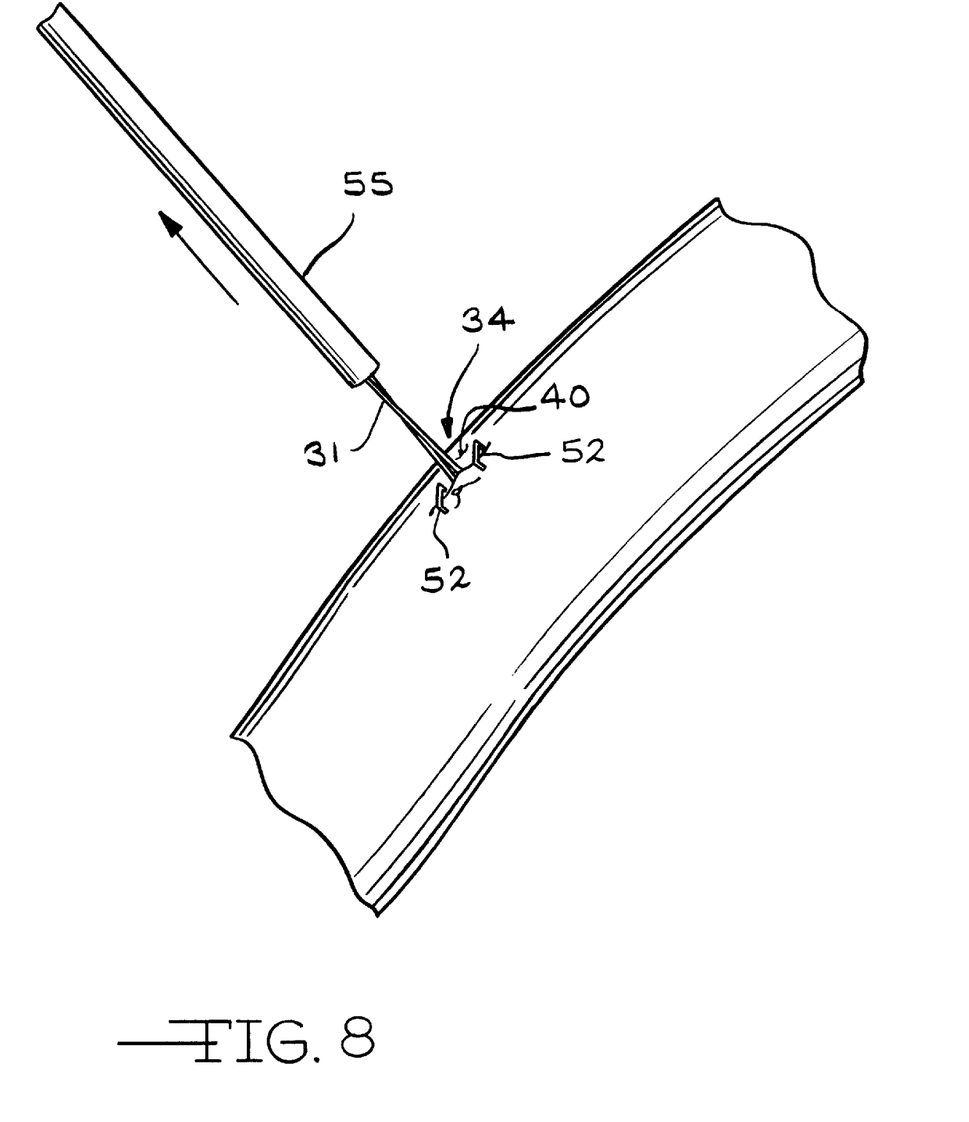
FIG. 8 is a perspective view of the tubular member and the guide wires being removed from the arterial opening; and, FIG. 9 is a perspective view of the closed artery wall after the apparatus of the present invention has been completely removed.

In FIG. 8, the tubular member 55 has been removed completely from the artery 10. The projections 40 on the guide wires 31 have been straightened by operation of the tubular member 55 and thus are capable of being removed from the opening 43.

Figure 9:
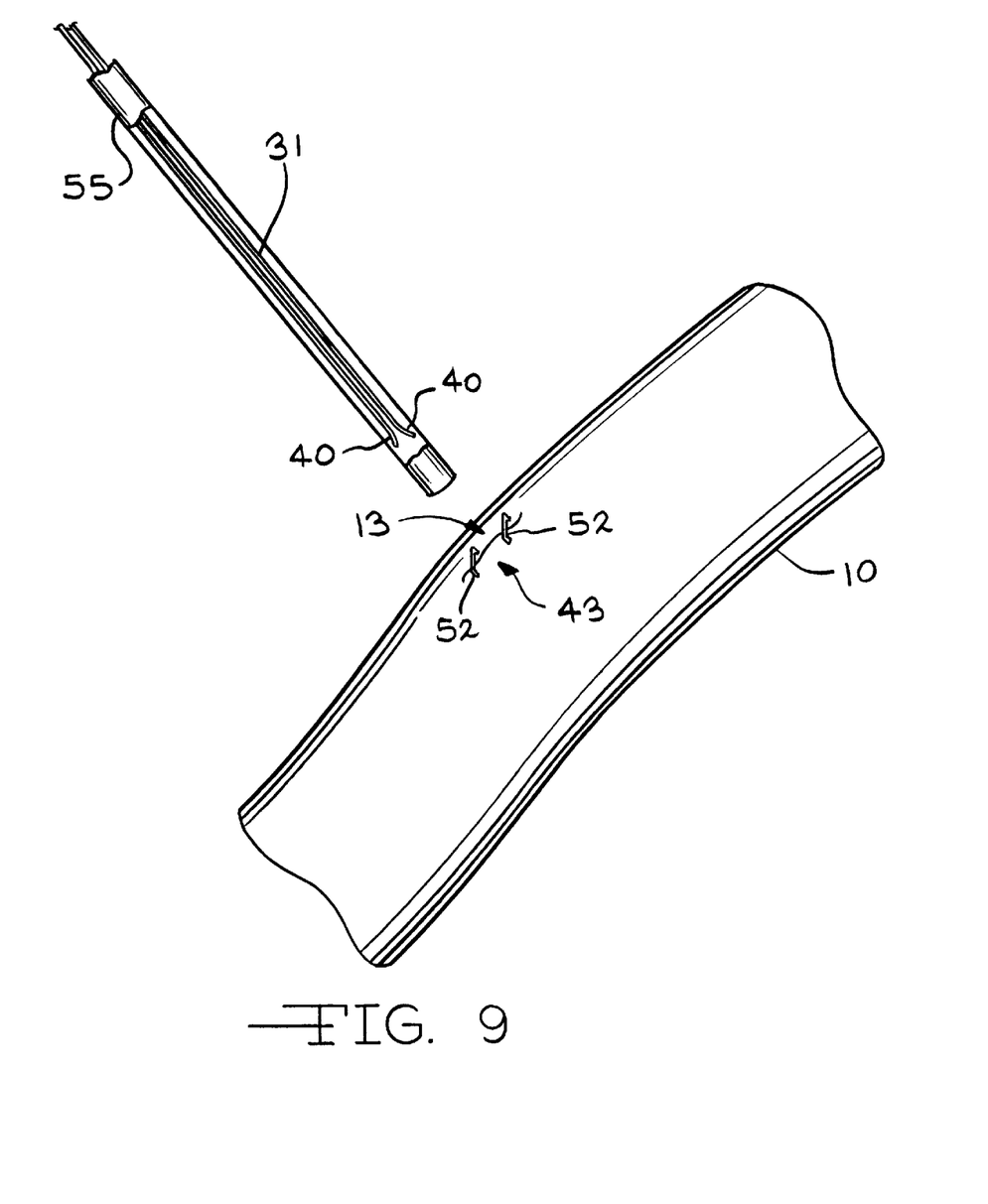

Turning to FIG. 9, the tubular member 55 and the guide wires 31 have been removed completely from the artery 10. The staples 52 approximate the arterial puncture 13 and the skin incision (not shown) can be closed with ordinary staples.

In operation, the method of the present invention comprises the following steps. First, the triple lumen catheter 19 is inserted into the artery 10 by threading the guide wire 16 through the third lumen 28. Once the catheter 19 has entered the artery 10 through the arterial puncture 13, the guide wires 31 are extended out of the catheter 19 into the inside of the artery 10. Next, the catheter 19 is removed from the inside of the artery 10.

The projections 40 are then engaged with the inside wall 11 of the artery 10 on opposite sides of the arterial puncture 13. Next, the guide wires 31 are twisted to close the opening 43 created by the arterial puncture 13. A vascular stapler 46 is introduced over the guide wires 31 by means of an eyelet 49. The friction generated between the eyelet 49 and the guide wires 31 urges the guide wires 31 toward each other which causes the sides of the arterial puncture 13 to be brought closer.

After the vascular stapler 46 is guided to the outside of the arterial puncture 13 and the position is verified by X-Ray or other detection means, the arterial puncture 13 is closed by inserting staples 52 into the arterial tissue around the opening 43.

The guide wires 31 are then removed by first passing a tubular member 55 over the guide wires 31. Sliding the tubular member 55 over the guide wires 31 causes the tubular member 55 to straighten the projections 40.

Once the projections 40 have been straightened or brought into alignment with the body 37 of the guide wires 31, the tubular member 55 and the guide wires 31 are removed from the arterial puncture 13. Finally, the incision in the skin is closed with normal staples (not shown).

The present invention offers several advantages including the prevention of bleeding and false aneurysms after arterial catheterization.

Another advantage is that the percutaneous method for arterial closure is much less costly than the typical surgical procedure because of the additional staff and equipment that are associated with surgical procedures.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. An apparatus for percutaneous arterial closure, comprising:

a) a catheter having at least one lumen;

b) at least two guide wires, each having a projection and disposed inside of the lumen with the projections extending in spaced apart directions;

c) a vascular stapler having an opening defined therein capable of receiving the at least two guide wires; and d) a tubular member capable of sliding over the guide wires.

2. The apparatus of claim 1, wherein the projection on the at least two guide wires is j-shaped.

3. The apparatus of claim 1, wherein the at least two guide wires are substantially parallel.

4. The apparatus of claim 1, wherein the at least two guide wires are coaxial.

5. The apparatus of claim 1, wherein the projections on the at least two guide wires extend in generally opposite directions.

6. The apparatus of claim 1, wherein the catheter is cylindrical and defines an interior space.

7. The apparatus of claim 1, wherein the catheter has at least three lumens and each of the guide wires is capable of being disposed inside one of the at least three lumens.

8. The apparatus of claim 7, wherein two of the at least three lumens are cylindrical and disposed inside the catheter and disposed opposite from one another.

9. The apparatus of claim 8, wherein the third of the at least three lumens is defined by the space remaining inside the catheter.

10. The apparatus of claim 1, wherein the at least two guide wires are deformable.

11. The apparatus of claim 1, wherein the opening on the vascular stapler encloses the at least two guide wires and urges the at least two guide wires toward each other.

12. An apparatus for percutaneous arterial closure, comprising:

a) a catheter defining an interior space and having at least three lumens, two of the at least three lumens being cylindrical and disposed on opposite sides of the inside of the catheter, a third one of the lumens defined by the space remaining inside the catheter;

b) at least two guide wires having a deformable projection, each of the guide wires capable of being disposed inside one of the at least three lumens;

c) a vascular stapler having an opening capable of receiving the guide wires; and d) a tubular member capable of sliding over the at least two guide wires.

13. The apparatus of claim 12, wherein the projection on the at least two guide wires is j-shaped.

14. The apparatus of claim 12, wherein the at least two guide wires are substantially parallel.

15. The apparatus of claim 12, wherein the at least two guide wires are coaxial.

16. The apparatus of claim 12, wherein the opening on the vascular stapler is formed by an eyelet.

17. A method of percutaneous arterial closure where catheterization has been concluded and a guide wire remains inside an artery having an arterial puncture, the method comprising the steps of:

a) providing a catheter having at least one lumen;

b) providing at least two guide wires having deformable projections extending therefrom;

c) inserting the at least two guide wires into the lumen of the catheter with the projections extending in spaced apart directions;

d) inserting the catheter into the artery by threading the guide wire through the lumen;

e) extending the at least two guide wires out of the catheter into the inside of the artery;

f) removing the catheter from the inside of the artery;

g) engaging the projections on the at least two guide wires with the inside surface of the artery around the arterial puncture;

h) twisting the at least two guide wires to close the puncture;

i) sliding a vascular stapler over the at least two guide wires;

j) stapling the arterial puncture;

k) providing a tubular member sized to fit over the at least two guide wires;

l) sliding the tubular member over the at least two guide wires such that the tubular member straightens the projections;

m) removing the tubular member and the guide wires from the arterial puncture; and, n) closing the opening in the skin.

18. The method of claim 17, including providing the projections on the at least two guide wires extending in generally opposite directions.

19. The method of claim 17, including providing the catheter having at least three lumens, wherein each of the guide wires is capable of being disposed inside one of the at least three lumens.

* * * * *